United States Patent [19]   [11] Patent Number: 5,075,337
Cordi et al.   [45] Date of Patent: Dec. 24, 1991

[54] ALPHA-DEUTERATED 2-ALKYLAMINOACETAMIDE DERIVATIVES HAVING REDUCED TOXICITY FOR TREATMENT OF CNS DISORDERS

[75] Inventors: Alex A. Cordi, St. Louis, Mo.; Philippe Janssens de Varebeke, Bossut-Gottechain; Hugo Gorissen, Grez-Doiceau, both of Belgium

[73] Assignee: G. D. Searle & Co., Chicago, Ill.

[21] Appl. No.: 385,632

[22] Filed: Jul. 26, 1989

[51] Int. Cl.$^5$ .................. A61K 31/16; A61K 31/165; A61K 31/17; C07C 237/00
[52] U.S. Cl. .................. 514/626; 514/237.5; 514/237.8; 514/238.8; 514/255; 514/313; 514/330; 514/331; 514/423; 514/426; 514/428; 514/594; 514/616; 514/620; 544/164; 544/168; 544/382; 544/390; 544/400; 546/224; 546/226; 546/232; 546/244
[58] Field of Search .................. 514/620, 626; 564/155-165, 194, 198

[56] References Cited

U.S. PATENT DOCUMENTS 4,639,468  1/1987  Roscucci et al. .................. 514/620

OTHER PUBLICATIONS

M. I. Blake et al., *J. Pharm. Sci.*, 64, 3, pp. 367-391 (1975).
A. B. Foster et al., *Advances in Drug Research*, vol. 14, pp. 2-36, Academic Press, London, (1985).
A. G. Goodman et al., *Basis of Therapeutics*, 7th Edn., p. 15, Mac Millan & Co., New York (1985).
P. L. Dostert et al., *Med. Res. Rev.*, 9, 45-89 (1989).
L. E. Dyck et al., *N. S. Arch. Pharm.*, 337, 279-283 (1988).

*Primary Examiner*—Mary C. Lee
*Assistant Examiner*—Fiona T. Powers
*Attorney, Agent, or Firm*—J. Timothy Keane; Paul D. Matukaitis

[57] ABSTRACT

Deuterated 2-alkylaminoacetamide compounds are described having the alpha carbon of the alkyl side chain of the compounds substituted by one or two deuterium atoms. These compounds have pharmacokinetic properties which enable treatment of CNS diseases with lower toxic effects. These compounds are also useful in evaluating the metabolic fate of non-deuterated counterpart compounds. Of particular interest are compounds of Formula I:

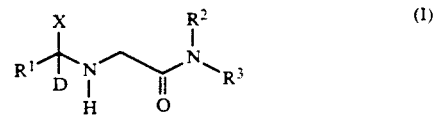

wherein X is deutero or hydrido; wherein $R^1$ is selected from alkyl and aralkenyl; wherein each of $R^2$ and $R^3$ is independently selected from hydrido and alkyl; wherein each of $R^1$, $R^2$ and $R^3$ having a substitutable position may be substituted with one or more halo radicals; or a pharmaceutically-acceptable salt thereof.

2 Claims, 1 Drawing Sheet

ALPHA-DEUTERATED 2-ALKYLAMINOACETAMIDE DERIVATIVES HAVING REDUCED TOXICITY FOR TREATMENT OF CNS DISORDERS

FIELD OF THE INVENTION

This invention is in the field of clinical neurology and relates specifically to compounds formulations and methods for treatment of central nervous system (CNS) disorders such as depression, Parkinson's disease, neurodegenerative ailments, schizophrenia, cognitive dysfunctions and epilepsy.

BACKGROUND OF THE INVENTION

Deuterated compounds have been used in pharmaceutical research to investigate the in vivo metaboic fate of the compounds by evaluation of the mechanism of action and metabolic pathway of the non-deuterated parent compound [M. I. Blake et al, *J. Pharm Sci*, 64, 3, 367-391 (1975)]. Such metaboic pathway studies are important in the design of safe, effective therapeutic drugs, either because the in vivo active compound often tends to be a metabolite of the parent compound administered to the patient, or because the metabolites produced from the parent compound prove to be toxic or carcinogenic [A. B. Foster et al, *Advances in Drug Research*, Vol. 14, pp. 2-36, Academic Press, London (1985)].

Most organs of the body are involved to some extent in the conversion of drugs yo meyabolic products. The liver, in particular, is the key organ involved in the metabolism of foreign substances, such as drugs, in the human body. Enzyme systems of the liver involved in the biotransformation of many drugs are primarily located in the smooth endoplasmic reticulum of the hepatocytes [A. G. Goodman et al, *Basis of Therapeutics*, 7th Edn, p. 15, MacMillan & Co., New York (1985)]. One particular enzyme of interest which is found in the liver, as well as other human organs such as the brain, is monoamine oxidase B-type (MAO-B) enzyme. This enzyme deaminates monoamine-containing compounds such as the neurotransmitters serotonin and dopamine. In the case of MAO-B enzymatic action, it is known that deuterium substitution on the carbon alpha to the amino moiety has a profound effect on the kinetics of oxidation [P. L. Dostert et al, *Med. Res. Rev.*, 9, 45-89 (1989)]. For example, the effect of deuteration of the compound phenelzine has been studied. It is known that phenelzine is metabolized in the peripheral system by the MAO-B enzyme, limiting its brain bioavailability. Deuteration of the carbon alpha to the hydazine moiety in phenelzine results in greater brain bioavailability of the compound by reduction of the peripheral metabolism [L. E. Dyck et al, N. S. Arch. Pharm., 337, 279-283 (1988)]. Another example of a compound having limited brain bioavailability is milacemide which is metabolized in the peripheral system by the MAO-B enzyme. The compound milacemide is described as 2-n-pentylaminoacetamide in U.S. Pat. No. 4,639,468 for control of epilepsy and depression and for memory enhancement treatment.

DESCRIPTION OF THE INVENTION

Figure 1:
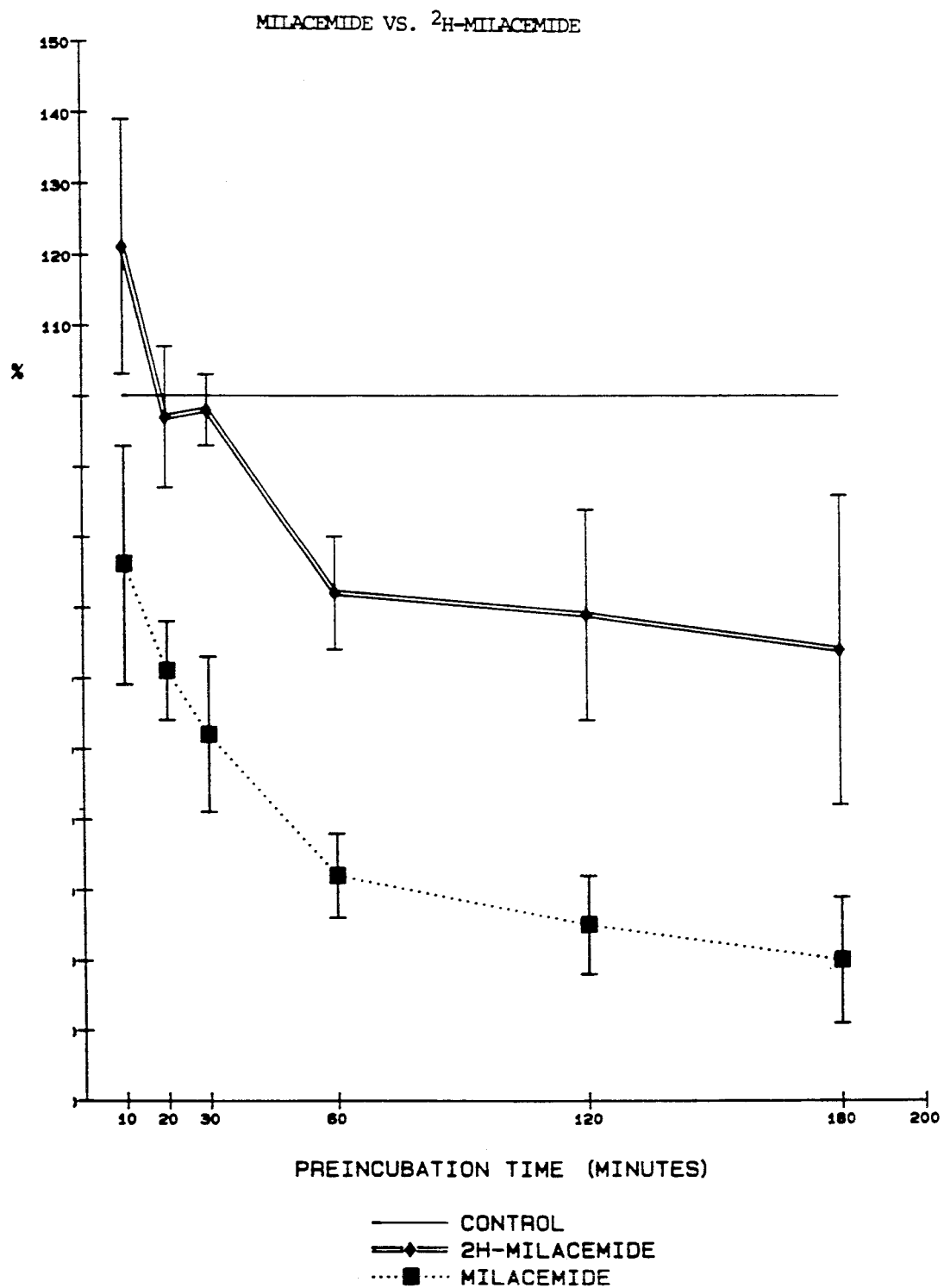
FIG. 1 is a graph comparing the inhbition of MAO-B enzyme by $^2$H-milacemide and by milacemide in rat mitrochondria.

Deuterated compounds useful in treatment of a CNS-realted disease, are provided by a family of deuterated compounds of Formula I:

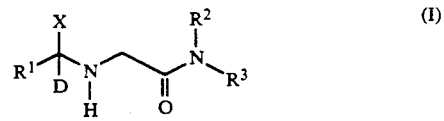

where X is deutero or hydrido; wherein R$^1$ is selected from alkyl, cycloalkyl, cycloalkylalkyl, aralkyl, aralkenyl, aryloxyalkyl and arylthioalkyl; wherein each of R$^2$ and R$^3$ is independently selected from hydrido, alkyl, cycloalkyl, cycloalkylalkyl, aralkyl, aralkenyl, aryloxyalkyl, arylthioalkyl,

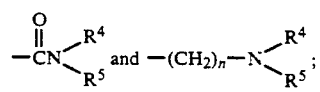

wherein each of R$^4$ and R$^5$ is independently selected from hydrido, alkyl, aralkyl, aryloxyalkyl and arylthioalkyl, and n has a value selected from zero through six, inclusive; wherein the groups R$^4$ and R$^5$ together with the nitrogen atom to which such groups are attached can form a five- or six-membered saturated heterocyclic ring containing one or two hetero atoms selected from oxygen and nitrogen, which heterocyclic ring may be further substituted with one or more alkyl radicals; wherein R$^2$ and R$^3$ together with the nitrogen atom of Formula I can form a five- or six membered saturated heterocylcic ring containing one or two heteroatoms selected from oxygen and nitrogen, which ehterocyclic ring may be further substituted with one or more alkyl radicals; wherein each of R$^1$, R$^2$ and R$^3$ having a substitutable position may be substituted with one or more radicals selected from halo, alkyl, alkenyl, alkynyl, haloalkyl, alkoxy, alkylthio, alkylsulfinyl and alkylsulfonyl; or a pharmaceutically-acceptable salt thereof.

A preferred class of compounds of Formula I consists of those compounds wherein X is deutero or hydrido; wherein R$^1$ is selected from alkyl, cycloalkyl, cycloalkylalkyl, aralkyl and aralkenyl; wherein each of R$^2$ and R$^3$ is independently selected from hydrodo, alkyl, cycloalkyl, cycloalkylalkyl, aralkyl, aralkenyl,

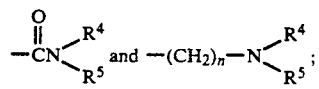

wherein each of R$^4$ and R$^5$ is independently selected from hydrido, alkyl and benzyl, and n has a value selected from zero through six, inclusive; wherein R$^2$ and R$^3$ together with the nitrogen atom of Fromula I can form a five- or six-membered saturated heterocyclic ring containing one or two hetero atoms selected from oxygen and nitrogen, which heterocyclic ring may be further substituted with one or more alkyl radicals; wherein each of R$^1$, R$^2$ and R$^3$ having a substitutable position may be substituted with one or more radicals selected for mhalo, alkyl, alkenyl, alkynyl, haloalkyl and alkoxy; or a pharmaceutically-acceptable salt thereof.

A more preferred class of compounds of Formua I consists of those compounds wherein X is deutero or hydrido; wherein $R^1$ is selected from alkyl, cycloalkyl, cycloalkylalkyl, aralkyl and aralkenyl; wherein each of $R^2$ and $R^3$ is independently selected from hydrido, alky, aralkyl,

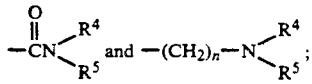

wherein each of $R^4$ and $R^5$ is independently selected from hydrido and alkyl, and n has a value selected from two through four, inclusive; wherein $R^2$ and $R^3$ together with the nitrogen atom of Formula I can form a five- or six-membered saturated heteroeyclic ring containing one or two hetero atoms, which heterocyclic ring is selected from pyrrolidinyl, piperidiny, piperazinyl and morpholino, and which heterocyclic group may be further substituted with one or more alkyl radicals; wherein each of $R^1$, $R^2$ and $R^3$ having a substitutable position may be substituted with one or more radicals selected from halo and alkyl or a pharmaceutically-acceptable salt thereof.

An even more preferred class of compounds wherein Formula I consists of those compounds wherein X is deutero or hydrido; wherein $R^1$ is selected from alkyl, aralkyl and aralkenyl, wherein each of $R^2$ and $R^3$ is independently selected from hydrido, alkyl aralkyl,

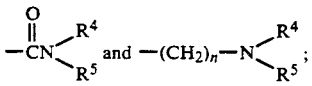

wherein each of $R^4$ and $R^5$ is independently selected from hydrido and alkyl, and n is two; wherein $R^2$ and $R^3$ together with the nitrogen atom of Formula I can form a five- or six-membered salurated heterocyclic group containing one or two hetero atoms, which heterocycic ring is selected from pyrrolivinyl, piperidinyl, piperazinyl and morpholino, and which heterocyclic group may be further substituted with one or more akyl radicals; wherein each of $R^1$, $R^2$ and $R^3$ having a substitutable position may be substituted with one or more halo radicals; or a pharmaceutically-acceptable salt thereof.

A highly preferred class of compounds within Formula I consists of those compounds wherein X is deutero or hydrido; wherein $R^1$ is selected from alkyl and aralkenyl; wherein each of $R^2$ and $R^5$ is independently selected from hydrido and alkyl; wherein each of $R^1$, $R^2$ and $R^3$ having a substitutable position may be substituted with one or more halo radicals; or a pharmaceutically-acceptable salt thereof.

A more highly preferred class of compounds within Formula I consists of those compounds wherein X is deutero; wherein $R^1$ is lower alkyl; wherein each of $R^2$ and $R^3$ is hydrido; or a pharmaceutically-acceptable salt thereof.

A group of specific highly preferred compounds within Formula I consists of:
2-(1,1-dideuteropentylamino)acetamide;
R-2-(1-deuteropentylamino)acetamide;
S-2-(1-deuteropentylamino)acetamide;
2-(cis-1,1-dideutero-3-phenyl-prop-2-enylamino) acetamide;
R-2-(cis-1-deutero-3-phenyl-prop-2-enylamino) acetamide;
S-2-(cis-1-deutero-3-phenyl-prop-2-enylamino) acetamide;
2-(trans-1,1-dideutero-3-phenyl-prop-2-enylamino) acetamide;
R-2-(trans-1-deutero-3-phenyl-prop-2-enylamino) acetamide;
S-2-(trans-1-deutero-3-phenyl-prop-2-enylamino) acetamide;
2-(1,1-dideuterooctylamino)acetamide;
R-2-(1-deuterooctylamino)acetamide;
S-2-(1-deuterooctylamino)acetamide;
2-(1,1-deuteroheptylamino)acetamide;
R-2-(1-deuteroheptylamino)acetamide;
S-2-(1-deuteroheptylamino)acetamide;
2-(1,1-dineutero-2-phenyethylamino)acetamide;
R-2-(1-deutero-2-phenyethylamino)acetamide;
S-2-(1-deutero-2-phenylethylamino)acetamide;
2-(1,1-dideutero-3-phenylpropylylamino)acetamide;
R-2-(1-deutero-3-phenylpropylamino)acetamide;
S-2-(1-deutero-3-phenylpropylamino)acetamide;
2-(1,1-dideutero-4-phenylbutylamino)acetamide;
R-2-(1-deutero-4-phenylbutylamino)acetamide;
S-2-(1-deutero-4-phenylbutylamjno)acetamide;
2-(1,1-dideutero-2-phenyloxyethalamino)acetamide;
R-2-(1-deutero-2-phenyloxyethylamino)acetamide;
S-2-(1-deutero-2-phenyloxyethylamino)acetamide;
2-(1,1-dideutero-2-propylpentylamino)acetamide;
R-2-(1-deutero-2-propylpentylamino)acetamide;
S-2-(1-deutero-2-propylpentylamino)acetamide;
2-[1,1-dideutero-3-(4-chlorophenyl)-propylylamino]acetamide;
R-2-[1,1-deutero-3-(4-chlorophenyl)propylamino]acetamide;
S-2-[1-deutero-3-(4-chlorophenyl)-propylamino]acetamino;
2-[1,1-dideutero-3-(3-methylphenyl)-propylylamino]acetamide;
R-2-1-deutero-3-(3-methylphenyl)propylamino]acetamide;
S-2-[1-deutero-3-(3-methylphenyl)propylamino]acetamide;
2-[1,1-dideutero-3-(2-methoxyphenyl)propyllamino]acetamide;
R-2-[1-deutero-3-(2-methoxyphenyl)-propylamino]acetamide;
S-2-[1-deutero-3-(2-methoxyphenyl)-propylamino]acetamide;
N-pentyl-N'-[2-(1,1-dideuteropentylamino)-1-oxoethyl]methylenediamine;
R-N-pentyl-N'-[2-(1-deuteropentylamino)-1-oxoethyl]-methylenediamine;
S-N-pentyl-N'-[2-(1-deuteropentylamino)-1-oxoethyl]-methylenediamine;
N-[2-(1,1-dideuteropentylamino)-1-oxoethyl]-1,2-ethylenediamine;
R-N-[2-(1-deuteropentylamino)-1-oxoethyl]-1,2-ethylenediamine;
S-N-[2-(1-deuteropentylamino)-1-oxoethyl]-1,2-ethylenediamine;
N-[2-(1,1-dideuteropentylamino)-1-oxoethyl]-1,2-propylenediamine;
R-N-[2-(1-deuteropentylamino)-1-oxoethyl]-1,3-propylenediamine;
S-N-[2-(1-deuteropentylamino)-1-oxoethyl]-1,3-propylenediamine;

N-[2-(1,1-dideuteropentylamino)-1-oxoethyl]-1,4-tetramethylenediamine;
R-N-[2-(1-deuteropentylamino)-1-oxoethyl]-1,4-tetramethylenediamine;
S-N-[2-(1-deuteropentylamino)-1-oxoethyl]-1,4-tetramethylenediamine;
N-[2-(1,1-dideuteropentylamino)-1-oxoethyl]-1,5-tetramethylenediamine;
R-N-[2-(1-deuteropentylamino)-1-oxoethyl]-1,4-tetramethylenediamine;
S-N-[2-(1-deuteropentylamino)-1-oxoethyl]-1,4-tetramethylenediamine;
N-[2-(1,1-dideuteropentylamino)-1-oxoethyl]-1,5-pentamethylenediamine;
R-N-[2-(1-deuteropentylamino)-1-oxoethyl]-1,5-pentamethylenediamine;
S-N-[2-(1-deuteropentylamino)-1-oxoethyl]-1,5-pentamethylenediamine;
N-[2-(1,1-dideuteropentylamino)-1-oxoethyl]-1,6-hexamethylenediamine;
R-N-[2-(1-deuteropentylamino)-1-oxoethyl]-1,6-hexamethylenediamine;
S-N-[2-(1-deuteropentylamino)-1-oxoethyl]-1,6-hexamethylenediamine;
N-methyl-N'-[2-(1,1-dideuteropentylamino)-1-oxoethyl]-1,2-ethylenediamine;
R-N-methyl-N'-[2-(1-deuteropentylamino)-1-oxoethyl]-1,2-ethylenediamine;
S-N-methyl-N'-[2-(1-deuteropentylamino)-1-oxoethyl]-1,2-ethylenediamine;
N-[2-(1,1-dideuteropentylamino)-1-oxoethyl]hydrazine;
R-N-[2-(1-deuteropentylamino)-1-oxoethyl]hydrazine;
S-N-[2-(1-deuteropentylamino)-1-oxoethyl]hydrazine;
N-[2-(1,1-dideuteropentylamino)-1-oxoethyl]piperazine;
R-N-[2-(1-deuteropentylamino)-1-oxoethyl]piperazine;
S-N-[2-(1-deuteropentylamino)-1-oxoethyl]piperazine;
N-[2-(4-morpholino)ethyl]-2-(1,1-dideuteropentylamino)acetamide;
R-N-[2-(4-morpholino)ethyl]-2-(1-deuteropentylamino)acetamide;
S-N-[2-(4-morpholino)ethyl]-2-(1-deuteropentylamino)acetamide;
N-[2-(4-morpholino)ethyl]-2-(1,1-dideutero-2-phenylethylamino)acetamide;
R-N-[2-(4-morpholino)ethyl]-2-(1-deutero-2-phenylethylamino)acetamide;
S-N-[2-(4-morpholino)ethyl]-2-(1-deutero-2-phenylethylamino)acetamide;
N-[2-(1,1-dideutero-4-phenylbutylamino)-1-oxoethyl]-1,2-ethylenediamine;
R-N-[2-(1-deutero-4-phenylbutylamino)-1-oxoethyl]-1,2-ethylenediamine;
S-N-[2-(1-deutero-4-phenylbutylamino)-1-oxoethyl]-1,2-ethylenediamine;
1-octyl-3-[2-(1,1-dideutero-2-phenylethyl)amino-1-oxoethyl]urea;
R-1-octyl-3-[2-(1-deutero-2-phenylethyl)amino-1-oxoethyl]urea;
S-1-octyl-3-[2-(1-deutero-2-phenylethyl)amino-1-oxoethyl]urea;
1-octyl-3-[2-(1,1-dideuterooctylamino)-1-oxoethyl]urea;
R-1-octyl-3-[2-(1-deuterooctylamino)-1-oxoethyl]urea;
S-1-octyl-3-[2-(1-deuterooctylamino)-1-oxoethyl]urea;
1-(2-phenylethyl)-3-[2-(1,1-dideutero-2-phenylethylamino)-1-oxoethyl urea;
R-1-(2-phenylethyl)-3-[2-(1-deutero-2-phenylethylamino)-1-oxoethyl urea;
S-1-(2-phenylethyl)-3-[2-(1-deutero-2-phenylethylamino)-1-oxoethyl urea;
1-(2-phenylethyl)-3-[2-(1,1-dideuterooctylamino-1-oxoethyl]urea;
R-1-(2-phenylethyl)-3-[2-(1-deuterooctylamino)-1-oxoethyl]urea;
S-1-(2-phenylethyl)-3-[2-(1-deuterooctylamino)-1-oxoethyl]urea;
1-pentyl-3-[2-(1,1-dideutero-2-phenylethyl)amino-1-oxoethyl]urea;
R-1-pentyl-3-[2-(1-deutero-2-phenylethyl)amino-1-oxoethyl]urea;
S-1-pentyl-3-[2-(1-deutero-2-phenylethyl)amino-1-oxoethyl]urea;

Most highly preferred of the foregoing group are the following compounds:
2-(1,1-dideuteropentylamino)acetamide;
R-2-(1-deuteropentylamino)acetamide; and
S-2-(1-euteropentylamino)acetamide.

Compounds of the general Formula I may be in the form of a salt of addition with a pharmaceutically utilizable acid, either an inorganic acid such as hydrochloric, hydrobromic, hydroiodic, nitric, carbonic, sufuric or phosphoric acid, or an appropriate organic acid such as an aliphatic, cycloaiphatic, aromatic, araliphatic, heterocyclic, carboxylic or sulphonic acid, including specific organic acids such as formic, acetic, proprionic, Succinic, gycolic, gluconic, lactic, malic, tartaric, citric, ascorbic, glucuronic, maleic, fumaric, pyruvic, aspartic, glutamic, benzoic, anthranilic, p-hydroxybenzoic, salicylic, phenylacetic, mandelic, embonic, methanesulphonic, ethanesulfonic, 2-hydroxyethanesulfonic, panthotenic, benzenesulfonic, toluenesulfonic, sulfanilic, mesylic, cyclohexylaminosulfonic, stearic, alginic, β-hydroxybutyric, malonic, galactaric and galacturonic The compounds of the general Formula can possess one or more asymmetric carbon atoms and are thus capable of existing in the form of different, pure optical isomers as well as in the form of racemic or non-racemic mixture thereof. All these forms fall within the scope of the present invention. The optical isomers can be obtained by resolution of the racemic mixtures according to conventional processes, for example, by formation of diastereoisomeric salts by treatment with optically active acid, such as tartaric, diacetyltartaric, dibenzoyltartaric, ditoluoyltartaric and camphorsulfonic acid, and separation of the mixture of diastereoisomers by crystallization followed by liberation of the optically active bases from these salts. A different process allowing the separation of optical isomers involves running a chiral chromatography column optimally chosen to maximize the separation of the enantiomers of the products of the invention or some derivatives thereof. Still another available method is to synthesize covalent stereoisomeric molecules by reacting the compounds of the invention with an optically pure acid in an activated form or with an optically pure isocyanate. The synthesized diastereoisomers can be separated by conventional means such as chromatography, distillation, crystallization or sublimation and submitted to an hydrolytic step which will deliver the enantiomericaly pure compound. The opticaly active compounds according to the general Formula I can likewise be obtained by utilizing optically active starting materials.

The present invention also covers pharmaceutical compositions containing, as active ingredient, at least one compound of the genera Formula I or its salt of addition with a pharmaceutically utilizable acid, in the presence or absence of suitable excipient.

These compositions are prepared in such a manner that they can be administered by oral, rectal, parental or local route. The compositions can be solids, liquids or gel and be utilized, according to the administration route, in the form of powders, tablets, lozenges, coated tabets, capsules, granulates, syrups, suspensions, emulsion solutions, suppositories or gels. These compositions can likewise comprise anolher therapeutic agent having an activity similar to or different from that of the compounds of the invention.

The term "hydrido" denotes a single hydrogen atom (H) which may be attached, for example, to an oxygen atom to form a hydroxyl group. Where the term "alkyl" is used, either alone or within other terms such as "haloalkyl", "aralkyl" or "hydroxyalkyl", the term "alkyl" embraces linear or branched alkyl radicals having one to about ten atoms. Preferred alkyl radicals are "lower alkyl" radicals having one to about five carbon atoms. The term "cycloalkyl" embraces radicals having three to ten carbon atoms, such as cyclopropyl, cyclobutyl, cyclopentyl, cycohexyl or cycloheptyl. The term "haloalkyl" embraces radicals wherein and one of more of the carbon is substituted with one or more halogen atoms, preferably selected from bromo, chloro and fluoro. Specificaly embraced by the term "haloalkyl" are monohaloalkyl, dihaloalkyl and polyhaloalkyl groups. A monohaloalkyl group, for example, may have either a bromo, a chloro or a fluoro atom within the group. Dihaloalkyl and polyhaloalkyl groups may be substituted by two or more of the same halo graup, or may have a combination of different halo atoms. Examples of polyhaloalkyl group are trifluoromethyl, 2,2,2-trifluoroethyl, perfluoroethyl and 2,2,3,3-tetrafluoropropyl grups. The term "thioalkyl", as represented by the fragment —SR, embraces radicals containing a linear or branched alkyl group, from one to about ten carbon length, linked to a divalent sulfur atom. The term "alkoxy", as represented by the fragment —OR, embraces linear or branched oxy-containing radicals having an alkyl portion of one to about ten carbon atoms, such as a methoxy, an ethoxy, an isopropoxy or a butoxy group. The term "aryl" embraces aromatic radicals such as phenyl, naphthyl and biphenyl. The term "heteroaryl" embraces heteroaromatic radicals such as pyridyl, quinolinyl, thienyl, furyl, imidazolyl and pyrrolyl. The term "aralkyl" embraces aryl-substituted alkyl radicals such as benzyl, diphenylmethyl, trityl, phenylethyl, phenylbutyl and diphenylethyl.

GENERAL SYNTHETIC PROCEDURES

The synthesis of compounds of general Formula I starts with preparation of the deuterated amine 2.

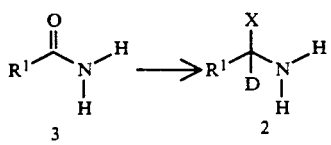

The more straightforward method is by reduction of the corresponding amide 3 with a metallic deuteride such as lithium aliuminum deuteride or a boro-deuteride such as deutero-diborane. The same reagetns can be used for the reduction of the corresponding nitrile 4.

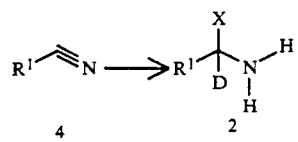

Or catalytic reduction with euterium gas in the presence of a noble metal catalyst such palladium, platinum or ruthernium could also provide the dideutero amine (X=D) starting from the correspondign nitrile 4.

In the case of the synthesis of the monodeutero-amine (X=H), a preferred starting material is the aldehyde 5 which can be directly subjected to reductive amination by mixign the aldehyde with an ammonium salt in he presence of a reductive agent, such as sodium cyanoborodeuteride or deuterium gas with palladium on carbon. Or by a stepwise process, the aldehyde is first condensed with an amine such as benzylamine (R*=CH$_2$—C$_6$H$_5$), and the amine 6 formed is then reduced by a metal deuteride as mentioned before, or by a boro-deuteride such as sodium borodueteride, or by deuterium gas in the presence of a catalyst. The protected duetero-amine 7 is then deprotected by conventional methods.

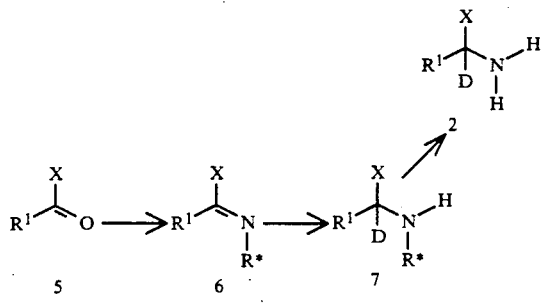

When X=H, the amine exists in two enantiomeric forms (R and S). Sterospecific synthesis of the R os S forms can be accomplished following the method described by A. R. Battersby et al [*J. Chem. Soc. Perkin I*, 2550 (1979)] wherein an enzyme is used to deliver sterospecifically the deuterium or the hydrogen atom onto the planar carbon atom. Other methods can be used to synthesize sterospecifically the desired enantiomer. For instance, the reductive step can be conducted in a chiral solvent such as (S,)-(+)-2,3-dimethoxy-1,4-bis(dimethylamino)butane. Or, in the case of deuterium gas reduction, the noble metal catalyst could be complexed by a chiral phosphine ligand, such as R,R,-DIOP or R,R,-DIPAMP. Or, in the case of the use of deuterides, a chiral ligand can induce sterospecificity, examples of such deuterides being chiral acyloxyborodeuterides, pinane derivatives of deutero-borane, and (2S, 3R)-(+)-4-dimethylamino-1,2-diphenyl-3-methyl-2-butanol complexes of lithium aliuminum hydrides. A last method which can be used to induce specific sterochemistry on the alpha carbon of 2 is by using in the third scheme presented a chiral amine (R* being a chiral residue) in an optically pure form such as R- or S-1-phenyl ethyl amine. In this scheme, the presence of the preexisting chirality will induce a steroselective reduction. Also, the formed intermediate will be a diastereomeric mixture which is likely to be amendable to separation into its constituent isomers by physical means such as chromatography or crystallization.

Methods useful for preparing compounds of general Formula I from amine 2 have been described in U.S. Pat. No. 4,639,468.

Process A

Conversion of amine 8 to a glycinamide of Formula I is as follows:

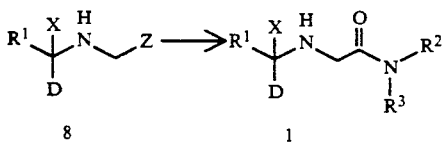

wherein $R^1$, $R^2$, and $R^3$ and X are as defined above, and Z is a function which by action of a suitable reactant may be transformed to an amide function. Examples of suitable reactants include carboxylic acid (—COOH), nitrile, (—CN), and ester of the formula (—COOR$^6$ wherein $R^6$ is a lower alkyl radical or a substituted phenyl radical so that it activates the ester with respect to attack by a nucleophile), an amidine of the formula:

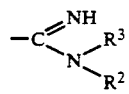

an acid halide function:

where Y represents a halogen atom such as chlorine or bromine, or an anhydride function. Z may also represent a carboxylic acid precursor such as, for example, trichloromethyl group or an oxazoline of the formula:

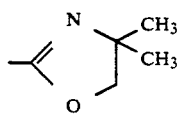

The passage of product 8 to product 1, namely, conversion of an amide precursor into amide, is made by any of the following reactions:

(a) Conversion of Carboxylic Acid into Amide

Several processes allow this chemical transformation to be made. For example, the carboxylic acid may be added to the amine, and the salt so formed may be transformed to the amide, and as well as by the action of a dehydrating agent, such as $P_2O_5$. Another way of proceeding consists of transforming the carboxylic acid into acid halide, then into amide by action of an amine. The conversion of he acid into acid halide may be done in absence of solvent with thionyl chloride, phosphorus pentachloride or phosphorus oxychloride. The corresponding bromides may also be used. In order for the reaction to be completed, it is often useful to heat the reaction mixture to a temperature between 50° and 0° C. If a sovent is used for the reaclion, it should be an inert orcanic solvent, such as benzene, toluene, petroleum ether, or ethers such as diethyl ether.

The reaction between acid halide and amine is carried out by cooling the reaction mixture to a temperature between 0° C. and −50° C., adding an amine excess (at least 2 equivalents, or at least 1 equivalent of amine and at least 1 equivalent of a tertiary orcanic base, such as triethylamine, per equivalent of acid haide). Usually, the acid choride is added to he amine as a solution in an inert organic solvent, such as those hereinabove defined, or as a solution in water.

Still another way of proceeding consists of reacting a carboxylic acid and an amine in the presence of a coupling agent such as used in peptide synthesis. Presently, a large number of coupling agents exist such as dicyclohexylcarbodiimide, N-ethyl-N'-3-dimethylaminopropylcarbodiimide, phosphenes, phosphates, silicium tetrachloride and titanium tetrachloride.

(B) CONVERSION OF NITRILE INTO AMIDE

The nitriles may be hydrolyzed into amides either in acid medium or in basic medium.

If hydrolysis is made under acid conditions, one may use concentrated sulfuric acid, aqueous concentrated hydrochloric acid, formic acid in the absence of solvent, or acetic acid in the presence of boron trifluoride. In most cases, it is advantageous to heat the reaction mixture at temperatures which may reach 200° C. Another way of conversion of a nitrile into amide, in acid medium, consists of treating said nitrile with hydrochloric acid in an alcohol such as ethanol An intermediate iminoether is thus formed, which is thermally transformed into amide.

If hydrolysis is made under basic conditions, in such a case an aqueous solution of a alkaline or alkaline-earth metal hydroxide is used. Advantageously, the presence of hydrogen peroxide improves the hydrolysis reaction. The nitrile may be hydrolyzed by adding 1 equivalent of cupric chloride to 1 equivalent of nitrile and conducting the reaction in an aqueous solution of an alkaline melal hydroxide at pH=10 and preferably at room temperature. The hydrolysis reaction may be carried out at a temperature between normal temperature and reflux temperature of the reaction mixture. Another method of basic hydroysis of nitries involves using an alkaline metal hydroxide, preferably potassium hydroxide in t-butanol.

(C) CONVERSION OF AN ESTER INTO AMIDE

Aminolysis of an ester may be conducted either in water or in an inert organic solvent. Example of usable solvents are aromatic hydrocarbons such as benzene and toluene, aliphatic hydrocarbons such as hexane and petroleum ether, and a halogenated hydrocarbons, such as dichoromethane and chloroform. The presence of a strong base may be essential in the case of reactions which are not very basic or which involve sterically hindered amines. The above reaction may be conducted at a temperature between room temperature and reflux temperature of the solvent.

(D) CONVERSION OF AMIDINE INTO AMIDE

The reaction is typically carried out by acid hydrolysis in aqueous or alcoholic medium. The acid may be inorganic such as hydrochloride acid or sulfuric acid, or orcanic such as acetic acid. The reaction takes place at a temperature between room temperature and reflux temperature of the reaction mixture.

When the group Z of the general formula 8 is a carboxylic acid precursor the transformation into carboxylic acid is made either in water, or in an inert organic solvent in the presence of acid. By inert organic solvent is meant a solvent such as an aromatic or aliphatic hydrocarbon, chlorinated or not, for example, benzene, toluene, chloroform, dichloromethane and ethers such as diethyl ether, tetrahydrofuran and dioxane. Acids which may be used are mineral aeids, such as halogen hydracids, concentrated or diluted sulfuric acid, concentrated or diluted nitric did and phosphoric acid, as well as organic acids such as acetic acid. The reaction temperature to be used is generally between 0° C. and 150° C., and preferably between 50° C. and 100°.

In some cases, it may be advantageous to convert Z into an amide by formation of an intermediate radical before generation of the amide function by the following procedures.

ACID-ESTER TRANSFORMATIONS

Acid and alcohol may be reacted in the presenee of an acid catalyst, such as hydrochloric acid or sulfuric acid or p-toluenesulfonic acid. This reaction is advantageously made under anhydrous conditions and one of the reactants should be used in a large excess. The solvent may be either one of the reactants, or an inert organic solvent such as chlorinated hydrocarbons, for example, chloroform or carbon tetrachoride or an aromatic or aliphatic hydrocarbon, such as benzene, toluene or petroleum ether. The temperature is between normal temperature and the reflux temperature of the reaction mixture.

Another way of proceeding consists of distilling out water as soon as formed by using a suitable apparatus. The reaction conditions are identical to those hereinabove described except that one of the reactants must not be used in a large excess.

The hydrolysis of the ester is made under similar conditions as for the esterification reaction but in this case, one of the reactants, water in this event, is used in a very large excess. The catalysis and temperature conditions are the same as for esterification.

TRANSFORMATION OF NITRILE INTO ESTER

The transformation of a nitrile into an ester is made by mixing the nitrile with an alcohol in acid medium as catalyst. Useful acid catalysts are hydrochloric acid, hydrobromic acid, hydroiodic acid, sufuric acid, p-toluenesulfonic acid and napthalenesulfonic acid. The alcohol may be used as a solvent or any other inert organic solvent may be used, such as chorinated hydrocarbons or aliphatic or aromatic hydrocarbons. The reaction may be run at a temperature between normal temperature and the reflux temperature of the solvent. An intermediate iminoether is thereby firmed, which is converted into ester by hydrolysis.

TRANSFORMATION OF NITRILE INTO ACID

The hydrolysis of a nitrile into carboxylic acid is carried out in acid medium or basic medium. As acid, generally a halogen hydracid is used such as hydrochloric acid or hydrobromic acid, or an oxacid such as sulfuric acid or nitric acid. As base, an alkaline hydroxide such as sodium hydroxide or potassium hydroxide is used. This hydroysis is carried out in water and under reflux for several hours.

TRANSFORMATION OF NITRILE INTO AMIDINE

The conversion of a nitrile into amidine is made by reacting the nitrile with an amine. It is often advantageous to activate one of the reagents so as to obtain amidine with a better yield. An activated form of nitrile may be an iminoether or an imino halide. The amine may be activated as a salt with an alkaline or alkaline-earth metal. Under these conditions, the amidines should be obtained with good yields.

Preferred methods for obtaining derivatives 8 are described hereinafter.

I. SYNTHESIS OF COMPOUND 8

1. The derivative 8 may be obtained from the product 9 by an alkylation reaction:

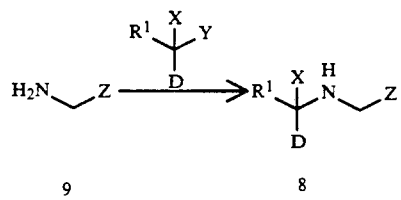

9      8 wherein $R_1$ is as previously defined, and Y represents a good nuceur fuje, such as a halogen, for example chlorine, bromine or iodine, a tosyl or mesyl group or an acyloxy group. The reaction may be made in an organic solvent, such as chloroform, dichloromethane, in an alcohol such as methanol or ethanol, or in a saturated or aromatic hydrocarbon, such as petroleum ether, benzene, toluene. The reaction is carried out either at room temperature or at a temperature between 0° C. and the reflux temperature of the solvent. Advantageously, the reaction may be made in the presence of an organic base, such as triethylamine, pyridine or N,N-dimethyaniline, or of an inorganic base, such as akaline or akaline-earth metal hydroxides, carbonates and bicarbonates or of finely pulverized lime. An example of this process is illustrated below:

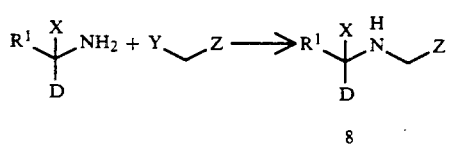

8

2. Another example of this process is when Z represents a nitrile (—CN) which may be schematized as follows:

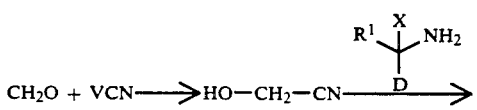

10

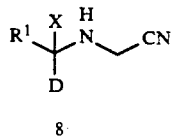

8 wherein $R^1$ is defined above and V represents a cation as more particularly defined below.

Cyanhydrin 10 used as co-reagent may be presynthetised or formed in situ from aldehyde ($CH_2O$) and an inorganic or organic cyanide, such as sodium or potassium cyanide or trimethylsilyl cyanide or alkyl aluminum or alkyl ammonium cyanide.

The condensation of the amine on cyanohydrin is made in inert organic solvent, such as chlorinated hydrocarbons, for example chloroform or dichloromethane, or an aromatic or aliphatic hydrocarbon, such as benzene, toluene of petroleum ether, or an ether such as deethyl ether or dioxane. In order to obtain a good yield, it is sometimes advantageous to work at a temperature between 20° C. and 120° C.

Acid may be used to catalyze the reaction, examples of such acids being a halogen hydracid such as hydrochloric acid, or an oxyacid, such as sulfuric acid, or an organic acid such as p-toluenesulfonic acid.

The reaction between an iminium salt 11 and a cyanide 12 occurs in the same way

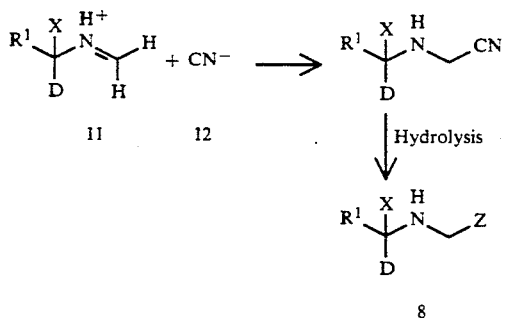

wherein R₁ and Z are as previously defined. The addition of ccanide 12 to the iminium salt 11 is made in an inert organic solvent, such as chlorinated hydrocarbons, for example chloroform or dichloromethane, or an aromatic or aliphatic hydrocarbon, such as benzene, toluene or petroleum ether. It is advantageous to operate at a temperature between 0° C. and the reflux temperature of the solvent. According to the hydrolysis conditions, Z will be a carboxylic acid, an amide, an ester or an amidine.

3. Another example of a method to obtain the derivative 8 is represented by the following scheme

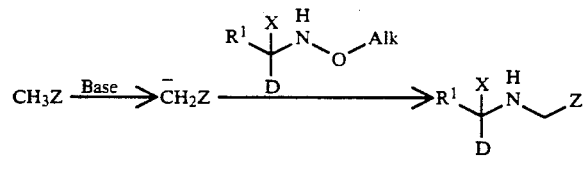

wherein R₁ and Z are as defined above and Alk represents a lower alkyl radical.

The derivative 13 is transformed into an anion 14 with a strong base in an inert organic solvent. The base may be an alkoxide, such as potassium t-butoxide, or an amide such as sodium or lithium amide, or a complex base, currently named "base of caubere" and which is a mixture of amide and alkoxide. The organic solvent is an aromatic or aliphatic hydrocarbon, such as benzene, toluene or petroleum ether. The reaction temperature may be between −20° C. and the reflux temperature of the solvent according to the reactivity of the substrate.

The anion of derivative 13 is then brought together with O-alkylated derivative of hydroxylamine 15 so as to form product 8. This substitution reaction is made in an inert orcanic solvent and at a temperature between −20° C. and the reflux temperature of the solvent.

II. SYNTHESIS OF COMPOUND 9

Reagent 9 which is a starting material in the synthesis of glycinamides of the invention may be obtained according to various methods.

1. A first synthesis method which involves Z as nitrile group (CN) is illustrated by the following scheme:

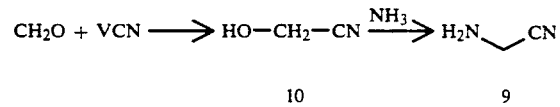

wherein V has the same meaning as described above. This process is very similar to the process described in paragraph I.2, the only difference being that the amine involved is in the present case ammonia instead of a primary amine. This difference is not critical for the definition of operation conditions so that conditions described in paragraph I.2 may be applied suceessfully for carrying out the present process.

2. Another method of obtaining derivative 3 which is similar to that which has been described in paragraph 1.3 may be schematized as follows:

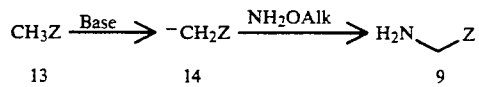

wherein Z is such as previously defined and Alk is a lower alkyl radical. The requirements as well for solvent as for base and temperature of this reaction have been defined in paragraph 1.3.

3. Another way of obtaining derivative 9 is characterized by formation of an intermediate imine 17 obtained from an amine and a carbonyl compound 16. The reduction of the imine leads to derivative 9.

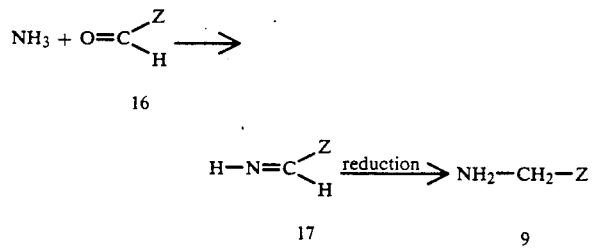

The condensation between the amine and carbonyl derivative 16 is usually made in an inert organic solvent, preferably water-immiscibe, such as benzene or touene. Advantageously, the reaction is catalysed by an organic or inorganic acid, such as p-toluenesulfonic acid. The imine so obtained is then reduced into amine. The reduction is made in the presence of hydrogen and hydrogenaled catalyst, such as platinum, platinum oxide or palladium on charcoal in a solvent such as methanoi, ethanol, ethyl acetate or glaeial acetic acid, at room temperature or more advantageously at a higher pressure, or still with an alkaline metal hydride such as sodium borohydride in a solvent such as methanol, or aluminum and lithium borohydride in a sovent such as ether or tetrahydrofuran. The reduction method of the imine will be selected so as to maintain intact the functionality of the group Z.

Another way of obtaining product 9, when Z represents a carboxy group (—COOH), uses an amine and glyoxal 18 according to the scheme

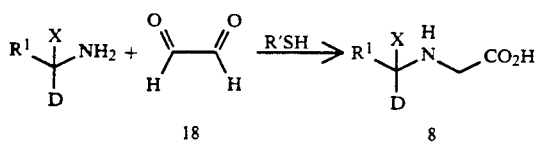

The oxydizing-reducing amination of the glyoxal 18 is made either in aqueous solution, or in an inert organic soivent selected for example from chlorinated hydrocarbons, such as chloroform or dichloromethane, or from lower alcohols, such as methanol or ethanol, or still from aromatic or aliphatic hydrocarbons, such as benzene, toluene or petroleum ester. The reaction is generally made at a temperature between room temperature and the reflux temperature of the solvent. Advantageously, a thiol (R α SH) will be added to the reaction mixture as catalyst (R' represents a lower alkyl radical $C_1$-$C_4$ or a phenyl ring).

PROCESS B

This process comprises hydrogenolysis of a sydnonimine 19 according to the following reaction scheme:

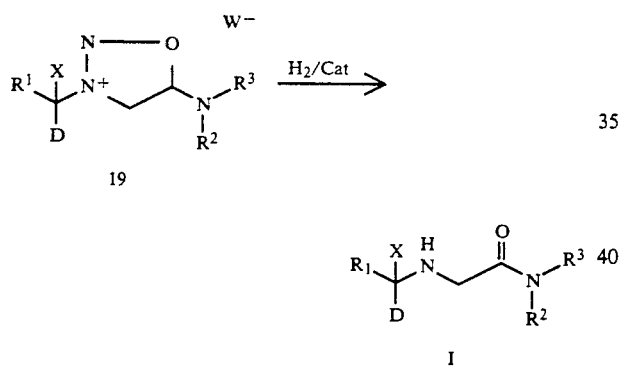

wherein $R^1$ is defined above and $W^\ominus$ represents an anion such as a halide, a sulfite, a nitrate, a phosphate or an anion deriving from an organic radical such as an acetate. The sydnonimine may be synthesized by various methods such as by spontaneous dehydration of N-nitroso-N-substituted aminonitrile. Hydrogenolysis of the sydnonimine leads to a 2-aminoacetamide. cataysts which may be used include palladium on active charcoal, nickel and platinum oxide. Generally, the catalyst is from the group of transition metals, their oxides or their sulfidee. The reaction solvent may advantageousy be methanol, ethanol, petroleum ether or any organic solvent which is inert in the reaction conditions. The reaction usually proceeds at room temperature but the temperature may be adapted to the molecule reactivity either by increasing or lowering it.

PROCESS C

According to this process, formaldehyde and an amine are introduced to an isonitrile in the presence of a carboxylic acid, as shown below:

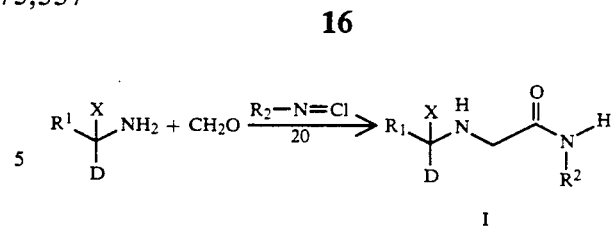

wherein $R^1$ and $R^2$ are as hereinabove defined. The condensation of the amine on the aldehyde is made under the same general conditions as for the imine synthesis. These conditions have been described in paragraph II.3. The addition of isonitrile is made in an inert organic solvent such as aromatic or aliphatic hydrocarbons, such as benzene, toluene or petroleum ether, or chlorinated hydrocarbons, such as chloroform or dichloromethane, or ethers, which are cyclic or not. The temperature at which the reaction may run is adapted to the reagent reactivity; if the reaetion is strongly exothermal, it may be useful to cool the reaction mixture in an ice bath or in a refrigerating bath based for example on dry ice; if on the contrary the reaction is very slow, it may be necessary to increase the temperature up to reflux.

A variant of this process involves firstly reacting formaldehyde and isonitrile 20 and then opening the intermediate imino-oxirane 21 by the amine, as shown below

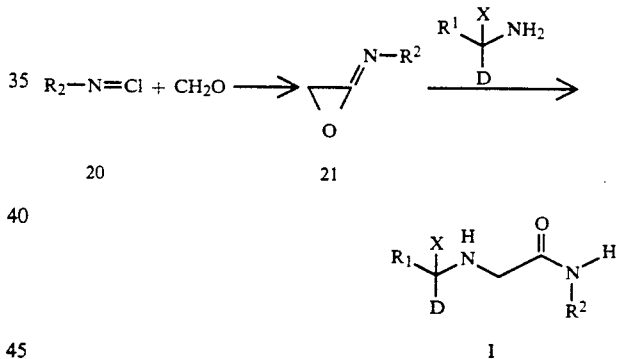

The reaction between aldehyde and isonitrile is preferably made at very ow temperature (between −30° C. and −100° C.) and is advantageously catalysed with a Lewis acid such as, for example, $BF_3$ etherate. An ether, such as diethylether, quite well meets the reaction requirements. To prevent any moisture trace, the reaction is made in a nitrogen or argon atmosphere. The opening of the imino-oxirane 21 is made by addition of amine to the reaction mixture at low temperature, then gradually raising the temperature to room temperature. The imino-oxirane 21 may also be synthesized by oxidation of centeimine 22, using m-chlorobenzoic acid (mCPBA) as the oxidizing agent, as shown below:

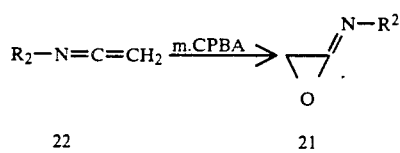

PROCESS D

In this process, amine 2 is reacted with glyoxal 18 so as to form a glycinamide, as shown below:

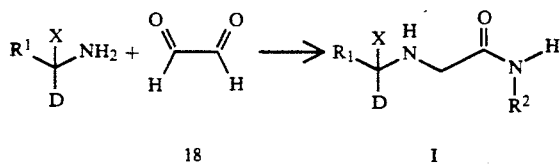

wherein $R^1$ is as previously defined, and $R^2$ is represented by

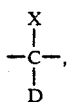

with $R^1$ and X as defined above. This reaction proceeds in two steps. First an exotheramal reaction develops when reagents are put into contact. Then, to obtain the desired glycinamide, the temperature of the reaction mixture or of the resulting solid has to be increased to about 150° C., advantageously until the reflux temperature is reached. This reaction proceeds without solvent or in an inert orcanic solvent, sueh as aromatic aliphatic hydrocarbons, such as benzene, toluene or petroleum ether, or in chlorinated solvents such as chloroform or carbon tetrachloride. If use of a base is necessary, an inorganic base will be preferably used, such as alkaline or alkaline-earth metal hydroxides or oxides, such as quick lime or sodium hydroxide, or a carbonate such as potassium carbonate.

Examples of the compounds of Formula I which can be synthesized in accordance with the foregoing general methods are as folows:

2-(1,1-dideuteropentylamino)acetamide;
R-2-(1-deuteropentylamino)acetamide;
S-2-(1-deuleropentylamino)acetamide;
2-(cis-1,1-dideutero-3-phenyl-prop-2-enyamino) acetamide;
R-2-(cis-1-deutero-3-phenyl-prop-2-enylamino) acetamide;
S-2-(cis-1-deutero-3-phenyl-prop-2-enylamino) acettamide;
2-(trans-1,1-dideutero-3-phenyl-prop-2-enylamino) acetamide;
R-2-(trans-1-deutero-3-phenyl-prop-2-enylamino) acetamide;
S-2-(trans-1-deutero-3-phenyl-prop-2-enylamino) acetamide;
2-(1,1-dideuteroocylamino)acetamide;
R-2-(1-deuterooctylamino)acetamide;
S-2-(1-deuterooctylamino)acetamide;
2-(1,1-dideuteroheptylamino)acetamide;
R-2-(1-deuteroheptylamino)acetamide;
S-2-(1-deuteroheptylamino)acetamide;
2-(1,1-dideutero-2-phenylethylamino)acetamide;
R-2-(1-deutero-2-phenylethylamino)acetamide;
S-2-(1-deutero-2-phenylethylamino)acetamide;
2-(1,1-dideutero-3-phenylpropylylamino)acetamide;
R-2-(1-deutero-3-phenylpropyamino)acetamide;
S-2-(1-deutero-3-phenylpropylamino)acetamide;
2-(1,1-dideutero-4-phenylbutylamino)acetamide;
R-2-(1-deutero-4-phenylbutylamino)acetamide;
S-2-(1-deutero-4-phenylbutylamino)acetamide;
2-(1,1-dideutero-2-phenyloxyeth-ylamino)acetamide;
R-2-(1-deutero-2-phenyloxyethylamino)acetamide;
S-2-(1-deutero-2-phenyloxyethylamino)acetamide;
2-(1,1-dideutero-2-propylpentylamino)acetamide;
R-2-(1-deutero-2-propylpentylamino)acetamide;
S-2-(1-deutero-2-propylpentylamino)acetamide;
2-[1,1-dideutero-3-(4-chlorophenyl)-propylylamino]acetamide;
R-2-[1-deutero-3-(4-chorophenyl)propylamino]acetamide;
S-2-[1-deutero-3-(4-chlorophenyl)propylamino]acetamide;
2-[1,1-dideutero-3-(3-methylphenyl)-propylylamino]acetamide;
R-2-[1-deutero-3-(3-methylphenyl)propylamino]acetamide;
S-2-[1-deutero-3-(3-methylphenyl)propylamino]acetamide;
2-[1,1-dideutero-3-(2-methoxyphenyl)-propylylamino]acetamide;
R-2-[1-deutero-3-(2-methoxyphenyl)-propylamino]acetamide;
S-2-[1-deutero-3-(2-methoxyphenyl)-propylamino]acetamide;
N-pentyl-N'-2-(1,1-dideuteropentylamino)-1-oxoethy]-methyenediamine;
R-N-pentyl-N'-[2-(1-deuteropentylamino)-1-oxoethyl]-methylenediamine;
S-N-pentyl-N'-[2-(1-deuteropentylamino)-1-oxoethyl]-methylenediamine;
N-[2-(1,1-dideuteropentylamino)-1-oxoethyl]-1,2-ethylenediamine;
R-[2-(1-deuteropentylamino)-1-oxoethyl]-1,2-ethylenediamine;
S-N-[2-(1-deuteropentylamino)-1-oxoethyl]-1,2-ethylenediamine;
N-[2-(1,1-dideuteropentylamino)-1-oxoethyl]-1,3-propylenediamine;
R-N-[2-(1-deuteropentylamino)-1-oxoethyl]-1,3-propylenediamine;
S-N-[2-(1-deuteropentylamino)-1-oxoethyl]-1,3-propylenediamine;
N-[2-(1,1-dideuteropentylamino)-1-oxoethyl]-1,4-tetramethylenediamine;
R-N-[2-(1-deuteropentylamino)-1-oxoethyl]-1,4-tetramethylenediamine;
S-N-[2-(1-deuteropentylamino)-1-oxoethyl]-1,4-tetramethylenediamine;
N-[2-(1,1-dideuteropentylamino)-1-oxoethyl]-1,5-pentamethylenediamine;
R-N-[2-(1-deuteropentylamino)-1-oxoethyl]-1,5-pentamethylenediamine;
S-N-[2-(l-deuteropentylamino)-1-oxoethyl]-1,5-pentamethylenediamine;
2-(1,1-(dideuteropenlylamino)-1-oxoethyl]-1,6-hexamethylenediamine;
R-N-[2-(l-deuteropentylamino)-1-oxoethyl]-1,6-hexaethylenediamine;
S-N-[2-(1-deuteropentylamino)-1-oxoethyl]-1,6-hexamethylenediamine;
N-methyl-N'-[2-(1,1-dideuteropentylamino)-1-oxoethyl]-1,2-ethylenediamine;
R-N-methyl-N'-[2-(1-deuteropentylamino)-1-oxoethyl]-1,2-ethylenediamine;
S-N-methyl-N'-[2-(1-deuteropentylamino)-1-oxoethyl]-1,2-ethylenediamine;
N-2-(1,1-dideuteropentylamino)-1-oxoethyl]hydrazine;

R-N-[2-(1-deuteropentylamino)-1-oxoethyl]hydrazine;
S-N-[2-(1-deuteropentylamino)-1-oxoethyl]hydrazine;
N-[2-(1,1-dideuteropentylamino)-1-oxoethyl]piperazine;
R-N-[2-(1-deuteropentylamino)-1-oxoethyl]piperazine;
S-N-[2-(1-deuteropentylamino)-1-oxoethyl]piperazine;
N-[2-(4-morpholino)ethyl]-2-(1,1-dideuteropentylamino) acetamide;
R-N-[2-(4-morpholino)ethyl]-2-(1-deuteropentylamino) acetamide;
S-N-[2-(4-morpholino)ethyl]-2-(1-deuteropentylamino) acetamide;
N-[2-(4-morpholino)ethyl]-2-(1,1-dideutero2-phenylethylamino)acetamide;
R-N-[2-(4-morpholino)ethyl]-2-(1-deutero2-phenylethylamino)acetamide;
S-N-[2-(4-morpholino)ethyl]-2-(1-deutero2-phenylethylamino)acetamide;
N-[2-(1,1-dideutero-4-phenylbutylamino)-1-oxoethyl]-1,2-ethylenediamine;
R-N-[2-(1-deutero-4-phenylbutylamino)-1-oxoethyl]-1,2-ethylenediamine;
S-N-[2-(1-deutero-4-phenylbutylamino)-1-oxoethyl]-1,2-ethylenediamine;
1-octyl-3-[2-(1,1-dideutero-2-phenylethyl)amino-1-oxoethyl]urea;
R-1-octyl-3-[2-(1-deutero-2-phenylethylamino)-1-oxoethyl]urea;
S-1-octyl-3-[2-(1-deutero-2-phenylethylamino)-1-oxoethyl]urea;
1-octyl-3-[2-(1,1-dideuterooctylamino)-1-oxoethyl]urea;
R-1-octyl-3-[2-(1-deuterooctylamino)-1-oxoethyl]urea;
S-1-octyl-3-[2-(1-deuterooctylamino)-1-oxoethyl]urea;
1-(2-phenylethyl)-3-[2-(1,1-dideutero-2-phenylethylamino)-1-oxoethyl]urea;
R-1-(2-phenylethyl)-3-[2-(1-deutero-2-phenylethylamino)-1-oxoethyl]urea
S-1-(2-phenylethyl)-3-[2-(1-deutero-2-phenylethylamino)-1-oxoethyl]urea;
1-(2-phenylethyl)-3-[2-(1,1-dideuterooctylamino-1-oxoethyl]urea;
R-1-(2-phenylethyl)-3-[2-(1-deuterooctylamino-1-oxoethyl]urea;
S-1-(2-phenylethyl)-3-[2-(1-deuterooctylamino-1-oxoethyl]urea;
1-pentyl TM 3-[2-(1,1-dideutero-2-phenylethyl)amino-1-oxoethyl]urea;
R-1-pentyl-3-[2-(1-deutero-2-phenylethylamino)-1-oxoethyl]urea; and
S-1-pentyl-3-[2-(1-deutero-2-phenylethylamino)-1-oxoethyl]urea.

The following examples are detailed descriptions of the methods of preparation of compounds of Formula I. These detailed preparations fall within the scope of, and serve to exemplify, the above described general synthetic procedure which form part of the invention. The examples are presented for illustrative purposes only and are not intended as a restriction on the scope of the invention.

EXAMPLE 1

Synthesis of 1,1-dideuteropentylamine

In a three neek flask kept under an nitrogen atmosphere, LiAD$_4$ (10 g, 0.238 mole) was suspended in anhydrous ether (500 mL). To this suspension, valeronitrile (22.6 mL, 0.216 mole) was added dropwise at such a rate to maintain the ether gently refluxing. After the addition was completed, the reaction mixture was further refluxed for two hours. To the cold solution, water (10 mL) and 10% NaOH (30 mL) were then added and the ether was decanted. The solid was dissolved carefully in 70% NaOH (400 mL) and the aqueous phase was extracted with ether (3×100 mL). The different ether phases were pooled and dried over $K_2CO_3$. The ether was distilled under normal pressure and the amine was collected as a colorless liquid distilling at 102°–104° C.

EXAMPLE 2

Synthesis of 2-(1,1-dideuteropentylamino)acetamide

In an Erlenmeyer flask immersed in an ice bath, $Na_2S_2O_5$ (0.072 mole) was dissolved in water (20.3 mL). Formaldehyde (10%-in-water, 43.2 mL, 0.144 mole) was then added portionwise and the solution stirred for 1.5 hour. At room temperature, 1,1-dideuteropentylamine (11.4 g, 0.131 mole) was added, and the mixture was stirred at room temperature for 1.5 hour. Then KcN (9.35 g, 0.143 mole) was added at once and the mixture stirred for an additional 1.5 hour at room temperature. The solution was extracted with ether (150 mL+3×50 mL), and then the organic phase was dried over magnesium sulfate and evaporated. The yelow residue was evaporated at 45° C., under high vacuum (4 10$^{-2}$ mm Hg) into a flask cooled by a dry ice-acetone bath. To the frozen colorless liquid, conc. Hcl (1.9 mL) was added, and the mixture was brought to 0° C. for 2 hours and then kept overnight in cold storage. The slightly yellowish solution was added slowly to acetone (1.9 L), and the solid was filtered and dried. Melting point: 204°–206 C°.

| Elemental Analysis | C | N |
|---|---|---|
| calculated | 46.02 | 15.33 |
| found | 45.98 | 14.91 |

BIOLOGICAL EVALUATION

Treatment of a mammal afflicted by or susceptible to a CNS disorder is accomplished by administration of a therapeutically-effective amount of a compound of Formula I. The compounds were evaluated by in vitro and in vivo model assays to determine the pharmacoogical properties of such compounds and their likely suitability for use as therapeutic drugs in human subjects.

MAO-B ENZYME INHIBITION ASSAY

The effect of the compounds of the present invention on the catalytie activity of the monoamine oxidase enzyme (MAO-B) was assayed by the method of Fowler (Fowler C. J. and Oreland L., *Biochem. Pharmac.*, 29, 2225-33, 1980). Rat brain mitochondria were purified by a modification of the method of Dodd (Dodd Sprague Dawley rats of about 200 gr were decapitated and the brain was rapidly removed from the skull. Brains were homogenized with a glass-Teflon homogenizer in ice cold 0.32M sucrose (1/10, w/v). The homogenate was centrifuged at 2,400 g for 10 min at 4° C. The supernatant was centrifuged at 3,000 g for 10 min at 4° C. This last supernatant (8 ml) was poured into at tube containing 4 ml of 1.2M sucrose. The mitochondrial fraction is obtained after a centrifugation at 115,000 g for 30 min at 4° C. The mitochondrial pellet was suspended in 4 ml of 50 mM Na phosphate buffer and stored as aliquots at −30° C. The mitochondrial protein concentration was assessed by the method of Bradford (Bradford M.M., *Anal. Biochem.*, 72, 248–54, 1976). Aliquots of the mitochondrial fraction were preincubated with $^2$H-milacemide or milacemide (200 μM in 50 mM Na phosphate buffer pH8) for different time periods, the samples were diluted with the incubation buffer, centrifuged and the pellets were then used for the MAO assay. The enzymatic assay was performed in Eppendorf micro tubes (1.5 ml). The 100 μl total incubation volume contained 40 μl of 7 mM $^{14}$C-β-phenylethylamine, 20 μl of 50 mM Na phosphate buffer pH 8 and 40 μl of the pre-incubated mitochondrial fraction ( 0.2 mg protein/ml). The closed micro tubes were immediately shaken using a vortex and incubated during 4 min at 37° C. The reaction was stopped by adding 20 μl of 1.5 N Hcl into the tube placed in an ice bath. The deaminated products were extracted with 600 μl of a toluene-ethyl acetate mixture (water saturated) and strongly mixed during 30 sec. The two layers were separated by centrifugation (10.000 g) for 10 min. Then, 400μL of the organic layer were added to 4 ml of lumagel in a scintillation counting vial. Blank values are obtained by incubating the mitochondrial fraction with Hcl 1.5M. 100% values were obtained by omitting the pre-incubation step with the inhibitor As can be seen from FIG. 1, milacemide inhibited MAO-B activity by 50% in 30 min whereas $^2$H-milacemide needed at least 3 hours to reach the same level of inhibition (i.e., of 6 fold more time).

PREVENTION OF CHEMICALLY INDUCED CONVULSIONS

The anticonvulsive effect of a compound of the invention was examined for clonic, tonic convulsions and death induced by different convulsant agents, namely, 3-mercaptopropionic acid (3-MPA 120 mg/kg subcutaneously) and bicuculline (BIC, 0.6 mg/kg intravenously), (W. van Dorsser, D. Barris, A. Cordi and J. Roba; *Arch. Int. Pharmacodyn.*, 266: 239–249 (1983)). The compounds of the invention were administered orally at dosage of either 100 mg/kg (3-MPA) or 30 mg/kg (BIc) in a volume of 10 ml/kg. each to 5 mice, 30 minutes or 2 hours before convulsions were induced. Test mice used were male Swiss albino mice weighing 22–33 g, CD1, charles River, France, housed in group of 10 on a 12 hours light-dark cycle for at least 1 week before use, and fasted overnight. The number of mice protected against tonic convulsions and the number of dead mice were noted. The results are given as a score which represents the total number of mice protected by a dose of 100 mg/kg for two groups of 5 animals (3-MPA) or the percentage of mice protected by a dose of 30 mg/kg in 4 groups of 5 animals (BIC). Results are shown in Table I.

TABLE I

| Comparative anticonvulsant effect of milacemide and $^2$H-milacemide | | |
|---|---|---|
| | 3-MPA | BIC |
| | (% Protected) | |
| milacemide | 20 | 65 |
| $^2$H-milacemide | 10 | 45 |

COMPARATIVE PHARMACOKINETIC

A comparative pharmacokinetic study was conducted in the cynomolgus monkey (Macaca fascicularis) with a 1:1 mixture of milacemide and $^2$H-milacemide administered to 4 males and 4 females used in this study. One animal of each sex received the mixture either by the i.v. route at the dose of 30 mg/kg, or by the intragastric route at the dose of 30 mg/kg or 100 mg/kg, or 300 mg/kg. Plasma samples were drawn from the males and 0–24 hours urine samples were collected by the females. Preliminary determinations of milacemide in the urine samples were made by HPLC. Then, 2 mL of a saturated solution of sodium carbonate and an internal standard (2-hexylaminoacetamide)were added to aliquot urine samples which were brouqht to 5 ml by water addition if necessary and extracted twice with 20 mL chloroform. The combined chloroformic solutions were dried over anhydrous sodium sulfate and evaporated to dryness under vacuum. The residue was dissolved in 1 mL ethyl acetate, the solution was mixed thoroughly with 0.3 mL 0.01 N HcL, centrifuged at 3000 rpm for 5 minutes and the organic layer was eliminated by suction. The aqueous solution was made alkaline by the addition of 0.3 mL of 0 5M borate buffer at pH 9.3. Derivatization occurs by addition of 0.3 mL of a solution of fluorescamine in acetone (75 g/L), then 10 to 20 pL aliquots were injected on a 5 Bondapak C18 column eluted by a mixture of tetrahydrofuran, water and 0.5M borate buffer (2/6/2) adjusted to pH 8 by the addition of hydrochloric acid. Retention times were 6 min for milacemide, and 11 min for the internal standard. Analysis of the ratio of unchanged deutero milacemide versus milacemide, was performed by GC-MS Milacemide and $^2$H-milacemide extracted from plasma aliquots were transformed into their respective N-trifluoroacetylated nitrile by reaction with trifluoroacetic anhydride. After separation from the impurities, on a 3% OV 17 column, the mass spectra were obtained in the chemical ionization mode by ammonia on a Riber 10-10 B mass spectrometer. The compounds exhibited pseudo molecular ions M+NH4+ at m/z 240 and 242 respectively. Quantification was performed using selected ion monitoring (SIM) on the base peaks mentioned.

TABLE 2

| $^2$H-milacemide/milacemide ratio in urine and in plasma after dosing cynomolgus monkeys with a 1:1 mixture of $^2$H-milacemide and milacemide. | | |
|---|---|---|
| Dose/route | Urine 24 hours excretion | Plasma AUC* |
| 30 mg/kg i.v. | 3.1 | 2.6 |
| 30 mg/kg i.g. | 7.4 | 14.6 |
| 100 mg/kg i.g. | 5.2 | 9.2 |
| 300 mg/kg i.g. | 3.7 | 7.1 |

*AUC = Area Under the Curve (plasma cc versus time) is a measure of the biodisponibility of the compound.

From these results, it is apparent that the use of $^2$H-milacemide changed dramatically the pharmacokinetic profile of the molecule. The new molecule is now endowed with a reduced first pass effect, a prolonged half-life and a decreased metabolic clearance. The differences belween the milacemide and $^2$H-milacemide are more dramatic at the lowest i.e. dose.

Also embraced within this invention is a lass of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered ingravascularly, ingraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitabe daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. compounds indicated for prophylactic therapy wiill preferably be administered in a daily dose generaly in a range from about 0.1 mg to about 100 mg per kiogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medieal condition of the patient, the severity of the disease, the route of admingstration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oii, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method for treating a subject afflicted with or susceptible to a convulsive disorder, said method comrpising administering to the subject a therapeutically-effective amount of a deuterated compound having a reduced first pass effect as compared to the non-deuterated counterpart of said deuterated compound, said deuterated compound being 2-(1,1-dideuteropentylamino)acetamide or a pharmaceutically-acceptable salt thereof.

2. The method of claim 1 whereins aid convulsive disorder is epilepsy.

* * * * *